US011617775B1

(12) United States Patent
Huynh et al.

(10) Patent No.: US 11,617,775 B1
(45) Date of Patent: *Apr. 4, 2023

(54) GINSENG CANDY COMPOSITION CONTAINING THE BETEL LEAF EXTRACT

(71) Applicant: Nam Linh Huynh, Escondido, CA (US)

(72) Inventors: Tran Ky Huynh, Ho Chi Minh (VN); Nam Linh Huynh, Escondido, CA (US)

(73) Assignee: Tran Ky Huynh, Ho Chi Minh (VN)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,081

(22) Filed: May 5, 2022

Related U.S. Application Data

(63) Continuation of application No. 17/648,682, filed on Jan. 24, 2022, now Pat. No. 11,564,967.

(51) Int. Cl.

| | | |
|---|---|---|
| *A61K 36/67* | (2006.01) |
| *A61K 36/899* | (2006.01) |
| *A61K 36/9068* | (2006.01) |
| *A61K 36/53* | (2006.01) |
| *A61K 36/68* | (2006.01) |
| *A61K 36/752* | (2006.01) |
| *A61K 9/00* | (2006.01) |
| *A61K 36/54* | (2006.01) |
| *A61K 35/644* | (2015.01) |
| *A61K 36/82* | (2006.01) |
| *A61K 36/00* | (2006.01) |
| *A61P 31/14* | (2006.01) |
| *A61K 47/42* | (2017.01) |
| *A61K 31/05* | (2006.01) |
| *A61K 36/886* | (2006.01) |
| *A61K 36/61* | (2006.01) |
| *A61K 36/9066* | (2006.01) |
| *A61K 36/889* | (2006.01) |
| *A61K 36/484* | (2006.01) |

(52) U.S. Cl.
CPC ............ *A61K 36/67* (2013.01); *A61K 9/0053* (2013.01); *A61K 31/05* (2013.01); *A61K 35/644* (2013.01); *A61K 36/484* (2013.01); *A61K 36/53* (2013.01); *A61K 36/54* (2013.01); *A61K 36/61* (2013.01); *A61K 36/68* (2013.01); *A61K 36/752* (2013.01); *A61K 36/82* (2013.01); *A61K 36/886* (2013.01); *A61K 36/889* (2013.01); *A61K 36/899* (2013.01); *A61K 36/9066* (2013.01); *A61K 36/9068* (2013.01); *A61K 47/42* (2013.01); *A61P 31/14* (2018.01); *A61K 2236/331* (2013.01); *A61K 2236/333* (2013.01)

(58) Field of Classification Search
None
See application file for complete search history.

(56) References Cited

U.S. PATENT DOCUMENTS

| | | | | |
|---|---|---|---|---|
| 2015/0132271 A1* | 5/2015 | Chang | ....................... | A23L 2/02 |
| | | | | 426/573 |
| 2015/0132438 A1* | 5/2015 | Chang | ................... | A23L 29/284 |
| | | | | 426/94 |
| 2015/0190450 A1* | 7/2015 | Chang | .................... | A61K 8/987 |
| | | | | 424/59 |
| 2016/0316761 A1* | 11/2016 | Thompson | ............. | A01N 63/22 |

* cited by examiner

*Primary Examiner* — Michael Barker
*Assistant Examiner* — Randall O Winston

(57) ABSTRACT

A ginseng candy composition having effect of nourishing the body, strengthen the immune system, antibacterial, antiviral related to the respiratory tract, and SARS-CoV-2 virus-neutralizing efficacy of betel leaf extract/essential oil was increased by the combination with the one or two or more plant extracts/essential oils ingredients, 4-allylpyrocatechol (APC) ingredient, a ginseng extract ingredient, and ingredients other by predefined order and predetermined percentage by weight of each ingredient; wherein the plant extracts/essential oils ingredients including chinese liquorice (*Glycyrrhiza uralensis* Fisch.), liquorice (*Glycyrrhiza Glabra* L.), mint (*Mentha haplocalyx* Briq.), lemongrass (*Cymbopogon citratus, Cymbopogon winterianus* J., *Cymbopogon flexuosus* Stapf.).

14 Claims, 2 Drawing Sheets

GINSENG CANDY COMPOSITION CONTAINING THE BETEL LEAF EXTRACT

CLAIM OF PRIORITY

This application is a continuation application of application Ser. No. 17/648,682, entitled "Oral compositions containing extracts of a betel leaf and related methods", filed on Jan. 24, 2022. The patent application identified above is incorporated here by reference in its entirety to provide continuity of disclosure.

FIELD OF THE INVENTION

The invention relates to the field of food processing technology. In particular, the present invention relates to the hard candy products containing biologically active ingredients that synergistic effect to strengthen the immune system, antibacterial, antiviral related to the respiratory tract, including a betel leaf extract/essential oil, plant extracts/essential oils, a mixture of ginger-honey, a mixture of lemon-kumquat-cinnamon; a ginseng extract ingredient, and 4-allylpyrocatechol (APC) ingredient. More specifically, the present invention relates to a ginseng candy composition containing the betel leaf extract.

BACKGROUND ART

According to research documents, the betel leaf extract contains about 15 to 40 compounds. Depending on species, or different geographical regions, the betel leaf extract/essential oil includes the following 9 groups of substances: monoterpenes (such as terpinene, pinene, limonene, thujene, camphene, etc.), sesquiterpenes (such as cadinene, elemene, caryophyllene, cubebene, etc.), alcohols (linalol, terpineol, cadinol, etc.), aldehydes (such as decanal, etc.), acids (such as palmitic acid, etc.), oxides (such as Eucalyptol, etc.), phenols (such as eugenol, chavibetol, chavicol, etc.), phenolic ethers (such as methyl eugenol) and esters (eugenol acetate, chavibetol acetate, etc.). The main components of betel leaf extract/essential oil including phenolic compounds and derivatives (eugenol, chavibetol, eugenol acetate, chavibetol acetate, 4-allylpyrocatechol diacetate, 4-allylpyrocatechol) account for a high proportion of about 25%-60% by weight. Accordingly, research show that the betel leaf extract/essential oil have inhibitory activity, killing viruses, bacteria, fungi and protozoa. Besides, the SARS-CoV-2 virus neutralizer activity agent of the betel leaf extract/essential oil was tested at the Pasteur Institute in Ho Chi Minh City, with the following results: (a) Don't cytotoxic to Vero E6 cells; (b) Titers against virus SARS-CoV-2 used in the neutralization reaction is TCID50/0.1 mL: 10 5.5; and (c) Betel leaf extract/essential oil has the ability to neutralize the SARS-CoV-2 virus when exposed/exposed to the virus for 30 minutes. This conclusion is a premise for more complete research and development of bactericidal and antiviral products containing betel leaves extracts/essential oils, contributing to effective prevention of virus SARS-CoV-2 during the Covid-19 pandemic.

On the other hand, ginseng pharmacological efficacy is observed in as early as in the oriental herbal medicine, medical and civil food has been used extensively. Ginseng may be ginseng tea, ginseng powder, ginseng extract, ginseng candy, tablet and ginseng, ginseng extract in the form of a candy and the like have been developed in a variety of products commercially available. However, the existing ginseng health-care food has single effect and is difficult to meet the requirement of diversified health care of people, and the special smell of ginseng is also difficult to accept by partial eaters. Furthermore, the raw ingredients used are usually ginseng root is used more often than other parts such as leaf stem, although extracts from ginseng leaf-stem also contain similar active ingredients with pharmacological functions. Ginseng's leaf-stems are more readily available at a lower cost than its root. Ginseng leaf-stem extract also has anti-fatigue, anti-hyperglycemic, anti-obesity, anti-cancer, anti-oxidant and anti-aging properties. In normal use, ginseng leaf-stem extract is quite safe; adverse effects occur only when it is overdosed or is of poor quality. In addition, ginseng flower extract has have been historically used as both medicine and food to strengthen the body's immune system.

According to patent application No. PH22019000157U1, the invention refers to a process of producing candy utilizing betel leaves (*Piper betel*) comprises the following method: a) preparing of ingredients; b) washing of fresh betel (*Piper betel*) leaves in a running water; c) extracting of betel (*Piper betel*) leaves juice; d) cooking under moderate heat by stirring constantly until sugar dissolves; e) boiling of the mixture in the pot over medium to high heat until reaching the hard crack stage between 300-31° F.; f) removing from heat; g) adding peppermint extract; h) cooling down the mixture; i) molding in a molding cups; and j) packing the candies into a polyethylene bag.

According to patent application No. KR101657488 was granted on Sep. 23, 2013, in South Korea, the invention refers to a manufacturing method of honeyed red ginseng candy, and to the honeyed red ginseng candy manufactured thereby. More particularly, the manufacturing method of honeyed red ginseng candy comprises the following steps of: removing impurities from the surface of red ginseng, and cleaning the same; naturally drying the moisture on the surface of the washed red ginseng; immersing the dried red ginseng in honey, and sugaring the same at 40-50° C. for 1-4 hours; cooling the resultant product in a double boiler at 80-90° C. for 10-15 hours; completely cooling the resultant product, drying the same in a drier having an ultraviolet ray sterilization device at 35-40° C. for 10-13 hours at 60 Hz, and ripening the resultant product for 24 hours by naturally drying the same; ripening and drying the honeyed red ginseng in a drier at 30-40° C. for 10-14 hours at 70 Hz to have a water content of 25-30%; dicing the ripened the honeyed red ginseng; obtaining honeyed red ginseng candies by inserting 100 parts by weight of sugar, 300 parts by weight of water, 10-50 parts by weight of starch syrup, and diced honeyed red ginseng to an electric cooking pot, and boiling the resultant product.

According to patent application No. KR101978313 was granted on May 14, 2019, in South Korea, the present invention relates to a red ginseng candy composition and a method for producing a red ginseng candy using the same. The red ginseng candy composition comprises 10 to 20 wt % of sugar, 5 to 15 wt % of starch syrup, 5 to 15 wt % of water, 25 to 45 wt % of a red ginseng extract, 5 to 15 wt % of a Japanese apricot syrup, 5 to 15 wt % of green tea powder, and 5 to 15 wt % of matrimony vine powder, with respect to the total weight of the red ginseng candy composition. The method of the present invention comprises: a candy base producing step of heating sugar, starch syrup and water at a temperature of 140 to 170° C. to produce a candy base; a heating and concentrating step of adding a red ginseng extract and a Japanese apricot syrup to the candy base, and heating and concentrating the same at a temperature of 140 to 150° C. for 30 to 120 minutes; a particle dispersion step of adding green tea powder and matrimony vine powder to a concentrate obtained by the heating and concentrating step, focusing ultrasonic waves generated from an ultrasonic focusing device on the concentrate, and dispersing particles; and a molding step of injecting the concentrate into a frame to mold the same in a candy shape.

The above inventions meet the specific purposes and requirements of a technical solution. However, the disclosure of the invention does not the synergistic combination of activities between the betel leaf extract/essential oil, plant extracts/essential oils, 4-allylpyrocatechol (APC) ingredient, and the ginseng extract ingredient to nourish the body, strengthen the immune system, antibacterial, and antiviral related to the respiratory tract. At the same time, the mixing ingredients, the percentage (%) of each ingredient participating in the mixing and the method of performing the steps are also different.

Therefore, it is necessary to create a ginseng candy composition containing the betel leaf extract, which has health care effects such as strengthening the immune system, anti-aging, lowering blood lipids, and anti-fatigue.

Furthermore, it is necessary to create a ginseng candy composition containing the betel leaf extract/essential oil synergistically combines the biologically active of plant extracts/essential oils, 4-allylpyrocatechol (APC) ingredient, and the ginseng extract.

Finally, what is needed to provide a ginseng candy composition containing the betel leaf extract that includes simple steps, to replace complicated processing steps for ingredients that are ginseng to improve health according to traditional methods.

This invention provides solutions to achieve the above goals.

SUMMARY OF THE INVENTION

Accordingly, an objective of the present invention is to provide a ginseng candy composition containing the betel leaf extract from the process of forming a homogenous solution by mixing a ginseng extract ingredient with at least two different solutions comprising a sweetener solution, and an antibacterial, antiviral solution in a specific order with a defined percentage (%) of the total weight of a derived preparation containing antibacterial, antiviral effect.

Another objective of the present invention is to provide a sweetener solution comprises a sweetener ingredient, a water ingredient, and a Ingredient D; wherein the sweetener ingredient selected from the one or more of the following a refined sugar, a jaggery, a malt syrup, a starch molasses, a lactose, an alcohol sugar, an additional sweeteners; wherein the additional sweeteners selected from a sugar, a high intensity sweetener, a sugar substitute, or a combination thereof.

Another objective of the present invention is to provide a Ingredient D including a mixture of ginger-honey, and a mixture of lemon-kumquat-cinnamon.

Another objective of the present invention is to provide an antibacterial, antiviral solution comprises a 4-allylpyrocatechol (APC) ingredient, a plant extracts/essential oils ingredients, and a betel leaf extract/essential oil ingredient.

Another objective of the present invention is to provide a ginseng candy composition containing the betel leaf extract comprising a sweetener ingredient; a ginger juice ingredient; a honey ingredient; a lemon juice ingredient; a kumquat juice ingredient; a cinnamon ingredient; a 4-allylpyrocatechol (APC) ingredient, a plant extracts/essential oils ingredients; a betel leaf extract/essential oil ingredient; a ginseng extract ingredient; and the remainder is a water ingredient.

Another objective of the present invention is to provide a ginseng candy composition containing the betel leaf extract comprising the sweetener ingredient having 50%-70% by weight; the ginger juice ingredient having 0.5%-1.5% by weight; the honey ingredient having 2.5%-7.5% by weight; the lemon juice ingredient having 1.5%-2% by weight; the kumquat juice ingredient having 1.5%-2% by weight; the cinnamon ingredient having 0.3%-0.4% by weight; the 4-allylpyrocatechol (APC) having 0.16%-0.17% by weight; the plant extracts/essential oils ingredients having 0.5%-1.5% by weight; the betel leaf extract/essential oil ingredient having 0.5% by weight; the ginseng extract ingredient having 0.5% by weight; and the remainder is the water ingredient.

Another objective of the present invention is to provide a ginseng candy composition containing the betel leaf extract comprising the sweetener ingredient having 55%-65% by weight; the ginger juice ingredient having 1% by weight; the honey ingredient having 5% by weight; the lemon juice ingredient having 1.5% by weight; the kumquat juice ingredient having 1.5% by weight; the cinnamon ingredient having 0.3% by weight; the 4-allylpyrocatechol (APC) having 0.16% by weight; the plant extracts/essential oils ingredients having 0.9% by weight including 0.2% by weight of a lemongrass extracts/essential oil ingredient, 0.5% by weight of a mint extracts/essential oil ingredient, and 0.2% by weight of a chinese liquorice/liquorice extracts/essential oil ingredient; the betel leaf extract/essential oil ingredient having 0.5% by weight; the ginseng extract ingredient having 0.5% by weight; and the remainder is the water ingredient.

Yet another objective of the present invention is to provide a ginseng candy composition containing the betel leaf extract comprising a sweetener ingredient; a ginger juice ingredient; a lemon juice ingredient; a 4-allylpyrocatechol (APC) ingredient, a plant extracts/essential oils ingredients; a betel leaf extract/essential oil ingredient; a ginseng extract ingredient; and the remainder is a water ingredient.

In view of the foregoing, another objective of the present invention is to provide a ginseng candy composition containing the betel leaf extract comprising a sweetener ingredient having 50%-70% by weight; a ginger juice ingredient having 0.5%-1.5% by weight; a lemon juice ingredient having 1.5%-2% by weight; a 4-allylpyrocatechol (APC) having 0.16%-0.17% by weight; a plant extracts/essential oils ingredients having 0.5%-1.5% by weight; a betel leaf extract/essential oil ingredient having 0.5% by weight; a ginseng extract ingredient having 0.5% by weight; and the remainder is a water ingredient.

Another objective of the present invention is to provide a ginseng candy composition containing the betel leaf extract comprising the sweetener ingredient having 55%-65% by weight; the ginger juice ingredient having 1% by weight; the lemon juice ingredient having 1.5% by weight; the 4-allylpyrocatechol (APC) having 0.16% by weight; the plant extracts/essential oils ingredients having 0.9% by weight including 0.2% by weight of a lemongrass extracts/essential oil ingredient, 0.5% by weight of a mint extracts/essential oil ingredient, and 0.2% by weight of a chinese liquorice/liquorice extracts/essential oil ingredient; the betel leaf extract/essential oil ingredient having 0.5% by weight; the ginseng extract ingredient having 0.5% by weight; and the remainder is the water ingredient.

Another objective of the present invention is to provide the plant extracts/essential oils ingredients including chinese liquorice (*Glycyrrhiza uralensis* Fisch.), liquorice (*Glycyrrhiza Glabra* L.), mint (*Mentha haplocalyx* Briq.), lemongrass (*Cymbopogon citratus, Cymbopogon winterianus* J., *Cymbopogon flexuosus* Stapf.).

Finally, the purpose of the invention is to provide a ginseng candy composition containing the betel leaf extract having the ginseng extract ingredient extracted from a ginseng biomass, ginseng roots, ginseng stems, ginseng leaves, ginseng flowers, and ginseng fruits with seeds removed in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, Vietnamese ginseng (*Panax vietnamensis*).

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

According to the embodiment of the present invention, a ginseng candy composition containing the betel leaf extract from the process of forming a homogenous solution by mixing a ginseng extract ingredient with at least two different solutions comprising a sweetener solution, and an antibacterial, antiviral solution in a specific order with a defined percentage (%) of the total weight of a derived preparation containing antibacterial, antiviral effect. In the embodiment of the present invention, percent mass or percentage (%) by weight=(mass of solute/mass of solution)×100%. The unit of mass is usually grams, or kilograms. Mass percent is also known as the correct percentage by weight or w/w %. It should also be noted that the molar mass is also within the meaning of the invention. Molar mass is the total mass of all atoms in a mole of compound. Total all volume percentages add up to 100%.

Figure 1:
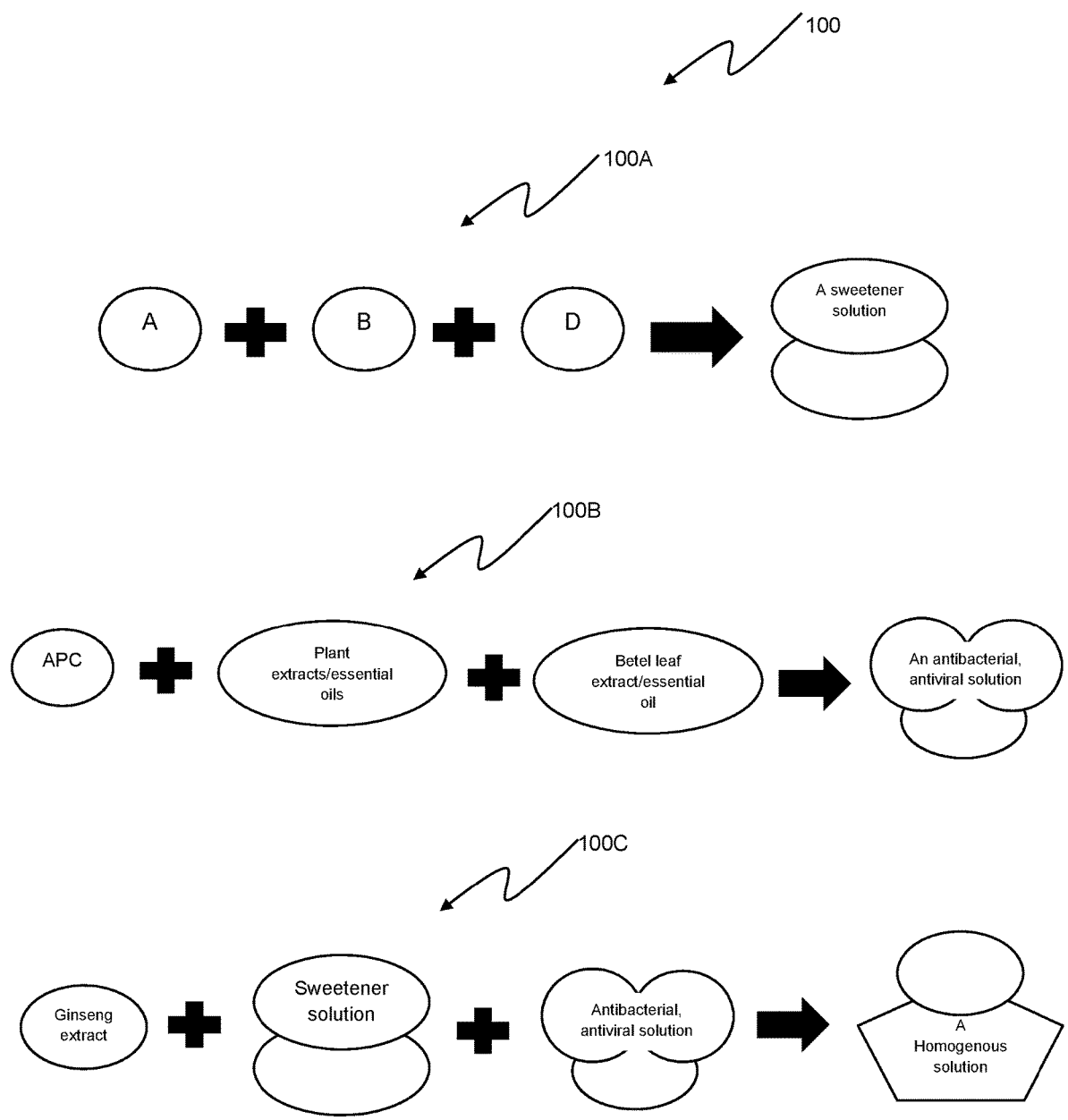
FIG. 1 is a conceptual block diagram illustrating the principle of making the ginseng candy composition containing the betel leaf extract in accordance with an exemplary embodiment of the present invention.

One embodiment of the invention is now described with reference to FIG. 1. FIG. 1 illustrates a conceptual block diagram of manufacturing the ginseng candy composition containing the betel leaf extract 100 ("method 100") in accordance with an exemplary embodiment of the present invention. Method 100 includes a first stage 100A to create the sweetening solution, a second stage 100B to create the antibacterial, antiviral solution, and a third stage 100C to create the homogenous solution.

In the first stage 100A, creating the homogeneous solution of at least three ingredients from ingredient A is a sweetener ingredient, ingredient B is a water ingredient, and a ingredient D is intended to dilute, prolong the time, increase antibacterial, prevention of sugar crystallization, and texturizing activity. However, in an exemplary embodiment of the present invention, ingredient A, ingredient B, and the ingredient D are added in a specific order with a defined percentage (%) by weight. Namely, ingredient A admixed first, then ingredient B, and finally ingredient D. It should be noted that when ingredient A, ingredient B, and ingredient D are not admixed in the specific order described, the final product will not have dilute, prolong the time, increase antibacterial, prevention of sugar crystallization, and texturizing activity.

According to the embodiment of the present invention, the sweetener ingredient selected from one or more of the following a refined sugar, a jaggery, a malt syrup, a starch molasses, a lactose, an alcohol sugar, an additional sweeteners; wherein the additional sweeteners selected from a sugar, a high intensity sweetener, a sugar substitute, or a combination thereof. According to the preferred embodiment of the present invention, the sweetener ingredient consists of 23% by weight of malt syrup. In addition, it should be noted that the term "water" in the embodiment of the present invention generally refers to water obtained by killing/removing or filtering microorganisms in water by means of high-temperature steam, UHT method, chemical method, ozone method, physical filtration method inorganic salts and similar substances in water are generally not reduced.

According to a preferred embodiment of the present invention, ingredient D is obtained by mixing two mixtures consisting of a mixture of ginger-honey, and a mixture of lemon-kumquat-cinnamon. Mixture of ginger-honey is obtained by mixing a ratio of a ginger juice ingredient and a honey ingredient having 1:5; wherein the ginger juice ingredient is selected from a ginger powder, or a ginger juice fresh, or a ginger extracts or a ginger pure juice is extracted and concentrated, or a ginger pure juice is extracted and concentrated at a temperature of 100° C.-110° C. According to the preferred embodiment of the present invention, the ginger juice ingredient is preferable to be obtained from a process consisting of the following steps:

(A) selecting and preparing ginger raw materials by a predetermined quality guideline and performing a visual inspection of said ginger that rough, branched, ridged skin, fibrous core, well-rounded ridges, and bright yellow, weighing 0.5-1 g, and free of spoilage spots;

(B) cleaning and chopping the ginger at step A to create a chopped ginger ingredient;

(C) distilling the chopped ginger ingredient at 40° C. for 3 hours in liquid water, or solvent, or brine solution, or saturated brine solution, or salt-free water/salt-free solution; to create a chopped and distilled ginger ingredient;
(D) collecting and cooling the chopped and distilled ginger ingredient;
(E) crushing and mechanically squeezing/squeezing to obtain ginger juice ingredient.

According to the embodiment of the present invention, the mixture of lemon-kumquat-cinnamon is obtained by mixing a ratio of a lemon juice ingredient:a kumquat juice:a cinnamon ingredient having 5:5:1. The cinnamon ingredient is selected from a cinnamon powder, or a cinnamon extracts or a cinnamon pure juice is extracted and concentrated, or a cinnamon pure juice is extracted and concentrated at a temperature of 100° C.-110° C. The lemon juice ingredient is selected from a lime juice, a lime pure juice, a lime juice fresh, a lemon pure juice, a lemon juice fresh, and mixtures thereof. The kumquat juice ingredient is selected from a kumquat pure juice, a kumquat juice fresh, and mixtures thereof.

It should be noted that the lemon juice ingredient, the kumquat juice ingredient replaced by a pure juice/juice fresh of citrus/citrus fruits including oranges (*Citrus sinensis*), grapefruits (*Citrus paradisi*), pomelo (*Citrus maxima/Citrus grandis*), lemons (*Citrus lemon*), limes (*Citrus aurantifoli*), Mandarin/Clementina/Tangerine (*Citrus reticulata* L.); all are listed in Table 1 below.

In another preferred embodiment of the present invention, ingredient D including the ginger juice ingredient, and the lemon juice ingredient; wherein the lemon juice ingredient replaced by a pure juice/juice fresh of citrus/citrus fruits including oranges (*Citrus sinensis*), grapefruits (*Citrus paradisi*), pomelo (*Citrus maxima/Citrus grandis*), lemons (*Citrus lemon*), limes (*Citrus aurantifoli*), Mandarin/Clementina/Tangerine (*Citrus reticulata* L.), kumquat (*Citrus japonica*); all are listed in Table 1 below.

In many aspects of the present invention, a sweetening solution obtained at the first stage 100A is defined as a solution with the following functions:
(a) sweetening solution is a solution that completely dissolves ingredient A, ingredient B, and ingredient D of a predetermined percentage (%) by weight;
(b) sweetening solution is a solution without the prevention of sugar crystallization;
(c) sweetening solution mixes act as a reactant, allowing the addition of ingredients to contribute their chemical and physical properties to create a new preparation;
(d) sweetening solution chemically bonds with the plant extracts/essential oils, betel leaf extracts/essential oils, 4-allylpyrocatechol (APC) ingredient, ginseng extract ingredient, and the composition of other supplements including but not limited to ionization reactions, covalent reactions, reducing reactions, replacement reactions, and rearrangement reactions to form a new chemical composition.

The term "homogeneous" is understood to mean the uniform distribution, or complete dissolution of, substances present in a solution/mixture.

Still with FIG. 1, continue to the second stage of 100B, creating the antibacterial, antiviral solution of at least three ingredients from a 4-allylpyrocatechol (APC) ingredient, a plant extracts/essential oils ingredients, and a betel leaf extract/essential oil ingredient of a predetermined percentage (%) by weight are intended to increase the antibacterial, antiviral effect. However, in an exemplary embodiment of the present invention, the ingredient 4-allylpyrocatechol (APC), the plant extract/essential oil component, and the betel leaf extract/essential ingredient is added in a particular order. Namely, the 4-allylpyrocatechol (APC) ingredient admixed first, then the plant extract/essential oil, and finally the betel leaf extract/essential oil. It should be noted that when 4-allylpyrocatechol (APC) ingredient, the plant extracts/essential oils, and betel leaf extracts/essential oils are not admixed in the specific order described, the final product will not have bactericidal, and antiviral related to the respiratory tract.

As the plant extract in the present invention, an "extracts/ essential" extracted as an aromatic substance contained in the above-mentioned plants is preferable. The essential oil in a narrow sense obtained by steam distillation from the above plants or dried materials thereof is preferably used as the "extracts/essential oil" in the present invention, but is not limited thereto. For example, oils extracted from the plants by using other methods such as extraction or expression are also included in the "extracts/essential oil" of the present invention as long as they contain essential oil components (such as aromatic substances). As other methods for extracting essential oils from plants, for example, solvent extraction (such as alcohol extraction, organic solvent extraction), oil and fat adsorption extraction (hot enfleurage or cold enfleurage), and supercritical fluid extraction are known. When the steam distillation cannot be applied because of a low essential oil content in the plant and the like, the solvent extraction is often used. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts/essential oil" in the present invention may be those in which the oil obtained by the above method is further purified and concentrated by using various purification procedures such as hydrophobic or adsorptive chromatography using a support such as porous beads, silica gel, or alumina.

According to the embodiment of the present invention, the betel leaf extract/essential oil ingredient and the 4-allylpyrocatechol (APC) ingredient extracted from fresh old betel leaves crushed/chopped/or not chopped, immersed are soaked in liquid water, or solvent, or brine solution, or saturated brine solution, or salt-free water/salt-free solution; wherein the total time from harvesting and preserving fresh old betel leaves from the betel nut tree must be less than 55 minutes; preferably 30-45 minutes.

According to the embodiment of the present invention, the plant extracts/essential oils ingredients selected from the one or more that including chinese liquorice (*Glycyrrhiza uralensis* Fisch.), liquorice (*Glycyrrhiza Glabra* L.), tea (*Camellia sinensis*), holy basil (*Ocimum sanctum*), turmeric (*Curcuma domestica*), clove (*Syzygium aromaticum*), aloe vera (*Aloe vera*), globe artichoke (*Cynara Scolymus* L.), roselle (*Hibiscus sabdariffa*), bitter melon (*Momordica charan*), basil (*Ocimum sanctum* L.), pomegranate (*Punica granatum* L.), chamber bitter (*Phyllanthus urinaria* L.), lemon balm (*Melissa officinalis*), mint (*Mentha haplocalyx* Briq.), horseradish tree (*Moringa oleifera* Lam.), white mulberry (*Morus alba* L.), ginger (*Zingiber officinale* Rosc), cinnamon (*Cinnamomum zeylanicum* Blume), broad-leaved plantain (*Plantago major* L.), areca nut palm (*Areca catechu* L.), apricot (*Prunus armeniaca* L.), lanxangia tsaoko (*Lanxangia tsaoko*), avocado (*Persea americana*), lemongrass (*Cymbopogon citratus, Cymbopogon winterianus* J., *Cymbopogon flexuosus* Stapf.), siamese ginger (*Alpinia officinarum*), red amaranth (*Amaranthus tricolor*), tufuling (*Smilax glabra* Roxb).

According to the preferred embodiment of the present invention, the plant extracts/essential oils ingredients including chinese liquorice (*Glycyrrhiza uralensis* Fisch.), liquorice (*Glycyrrhiza Glabra* L.), mint (*Mentha haplocalyx* Briq.), lemongrass (*Cymbopogon citratus, Cymbopogon winterianus* J., *Cymbopogon flexuosus* Stapf.).

According to the embodiment of the present invention, a ratio of the betel leaf extracts/essential oil and 4-allylpyrocatechol (APC) ingredient having 3:1.

In another preferred embodiment of the present invention, a ratio of the betel leaf extracts/essential oil and 4-allylpyrocatechol (APC) ingredient preferably having three parts of the betel leaf extracts/essential oil obtained from fresh, old betel leaves distilled with the saturated brine solution corresponds to one part of 4-allylpyrocatechol (APC) ingredient.

In another preferred embodiment of the present invention, a ratio of the betel leaf extracts/essential oil and 4-allylpyrocatechol (APC) ingredient preferably having three parts of the betel leaf extracts/essential oil obtained from fresh, old betel leaves distilled with the salt-free water/salt-free solution corresponds to one part of 4-allylpyrocatechol (APC) ingredient.

Finally, at the third stage of 100C, homogenous mixing a ginseng extract ingredient with the sweetener solution at stage 100A and the antibacterial, antiviral solution at stage 100B of a predetermined percentage (%) by weight, to create a homogenous solution. It should be noted that the term "admixed/mixed/admixing/mixing" as used in the present invention is understood to mean adding, or reacting, or dissolving homogeneously, or evenly, components in the same solution/mixture.

According to the embodiment of the present invention, the ginseng extract ingredient extracted from ginseng parts including ginseng roots, ginseng stems, ginseng leaves, ginseng flowers, and ginseng fruits with seeds removed that cleaned, then crushed/chopped/or not chopped and soaked in a liquid water, or solvent, or brine solution, or saturated brine solution, or salt-free water/salt-free solution. Ginseng root according to the embodiment of the invention having at least 6 years old; ginseng stems, ginseng leaves, ginseng flowers and ginseng fruits with seeds removed having at least 3 years old.

According to the embodiment of the present invention, the ginseng parts selected from the one or more in the genus *Panax* of the including *Panax notoginseng, Panax bipinnatifidus*; Korean ginseng, ginseng, red ginseng (*Panax ginseng*), *Panax japonicus*; American ginseng, Atlantic ginseng (*Panax quinquefolius*); Ngoc Linh ginseng, Vietnamese ginseng (*Panax vietnamensis*), *Panax wangianus, Panax zingiberebsis*, Himalayan ginseng (*Panax pseudoginseing*), *Panax stipuleanatus*. In another preferred embodiment of the present invention, the ginseng parts preferably selected from the one or more in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, Vietnamese ginseng (*Panax vietnamensis*).

According to the preferred embodiment of the present invention, the ginseng extract ingredient extracted from ginseng parts preferably selected from the one or more in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, Vietnamese ginseng (*Panax vietnamensis*).

In another embodiment of the invention, the ginseng extract ingredient further comprising extracted from a ginseng biomass in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, Vietnamese ginseng (*Panax vietnamensis*).

In another embodiment of the invention, the ginseng extract ingredient further comprising a commercial ginseng extract ingredients in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, Vietnamese ginseng (*Panax vietnamensis*).

In another embodiment of the invention, a ratio of the betel leaf extract/essential oil ingredient and the 4-allylpyrocatechol (APC) ingredient, and the ginseng extract ingredient having 3:1:3.

It should be noted that the term "ginseng candy containing the betel leaf extract composition" means "ginseng candy", "ginseng candy product", or "ginseng candy containing betel leaf extract product" according to the embodiment of the invention.

According to the embodiment of the present invention, the ginseng candy is made by method 100 depending on the percentages (%) of each of the ingredients listed in detail in Table 2 including formula 1 and formula 2, wherein formula 1 is stronger than formula 2; in which the comparative factor is bactericidal, and antiviral activity.

According, formula 1 comprising a sweetener ingredient; a ginger juice ingredient; a honey ingredient; a lemon juice ingredient; a kumquat juice ingredient; a cinnamon ingredient; a 4-allylpyrocatechol (APC) ingredient, a plant extracts/essential oils ingredients; a betel leaf extract/essential oil ingredient; a ginseng extract ingredient; and the remainder is a water ingredient. In another preferred embodiment of the present invention, the plant extracts/essential oils ingredients preferably including chinese liquorice (*Glycyrrhiza uralensis* Fisch.), liquorice (*Glycyrrhiza Glabra* L.), mint (*Mentha haplocalyx* Briq.), lemongrass (*Cymbopogon citratus, Cymbopogon winterianus* J., *Cymbopogon flexuosus* Stapf.).

According, formula 1 comprising a sweetener ingredient; a ginger juice ingredient; a lemon juice ingredient; a 4-allylpyrocatechol (APC) ingredient, a plant extracts/essential oils ingredients; a betel leaf extract/essential oil ingredient; a ginseng extract ingredient; and the remainder is a water ingredient. In another preferred embodiment of the present invention, the plant extracts/essential oils ingredients preferably including chinese liquorice (*Glycyrrhiza uralensis* Fisch.), liquorice (*Glycyrrhiza Glabra* L.), mint (*Mentha haplocalyx* Briq.), lemongrass (*Cymbopogon citratus, Cymbopogon winterianus* J., *Cymbopogon flexuosus* Stapf.).

According to the embodiment of the present invention, the percentage (%) of each ingredient that makes ginseng candy formula 1 comprises a sweetener ingredient having 50%-70% by weight; a ginger juice ingredient having 0.5%-1.5% by weight; a lemon juice ingredient having 1.5%-2% by weight; a 4-allylpyrocatechol (APC) having 0.16%-0.17% by weight; a plant extracts/essential oils ingredients having 0.5%-1.5% by weight; a betel leaf extract/essential oil ingredient having 0.5% by weight; a ginseng extract ingredient having 0.5% by weight; and the remainder is a water ingredient.

In another preferred embodiment of the present invention, formula 1 comprises the sweetener ingredient having 55%-65% by weight; the ginger juice ingredient having 1% by weight; the honey ingredient having 5% by weight; the lemon juice ingredient having 1.5% by weight; the kumquat juice ingredient having 1.5% by weight; the cinnamon ingredient having 0.3% by weight; the 4-allylpyrocatechol (APC) having 0.16% by weight; the plant extracts/essential oils ingredients having 0.9% by weight including 0.2% by weight of a lemongrass extracts/essential oil ingredient, 0.5% by weight of a mint extracts/essential oil ingredient, and 0.2% by weight of a chinese liquorice/liquorice extracts/essential oil ingredient; the betel leaf extract/essential oil ingredient having 0.5% by weight; the ginseng extract ingredient having 0.5% by weight; and the remainder is the water ingredient.

According to the embodiment of the present invention, the percentage (%) of each ingredient that makes ginseng candy formula 2 comprises a sweetener ingredient having 50%-70% by weight; a ginger juice ingredient having 0.5%-1.5% by weight; a lemon juice ingredient having 1.5%-2% by weight; a 4-allylpyrocatechol (APC) having 0.16%-0.17% by weight; a plant extracts/essential oils ingredients having 0.5%-1.5% by weight; a betel leaf extract/essential oil ingredient having 0.5% by weight; a ginseng extract ingredient having 0.5% by weight; and the remainder is a water ingredient.

In another preferred embodiment of the present invention, formula 2 comprises the sweetener ingredient having 55%-65% by weight; the ginger juice ingredient having 1% by weight; the lemon juice ingredient having 1.5% by weight; the 4-allylpyrocatechol (APC) having 0.16% by weight; the plant extracts/essential oils ingredients having 0.9% by weight including 0.2% by weight of a lemongrass extracts/essential oil ingredient, 0.5% by weight of a mint extracts/essential oil ingredient, and 0.2% by weight of a chinese liquorice/liquorice extracts/essential oil ingredient; the betel leaf extract/essential oil ingredient having 0.5% by weight; the ginseng extract ingredient having 0.5% by weight; and the remainder is the water ingredient.

Figure 2:
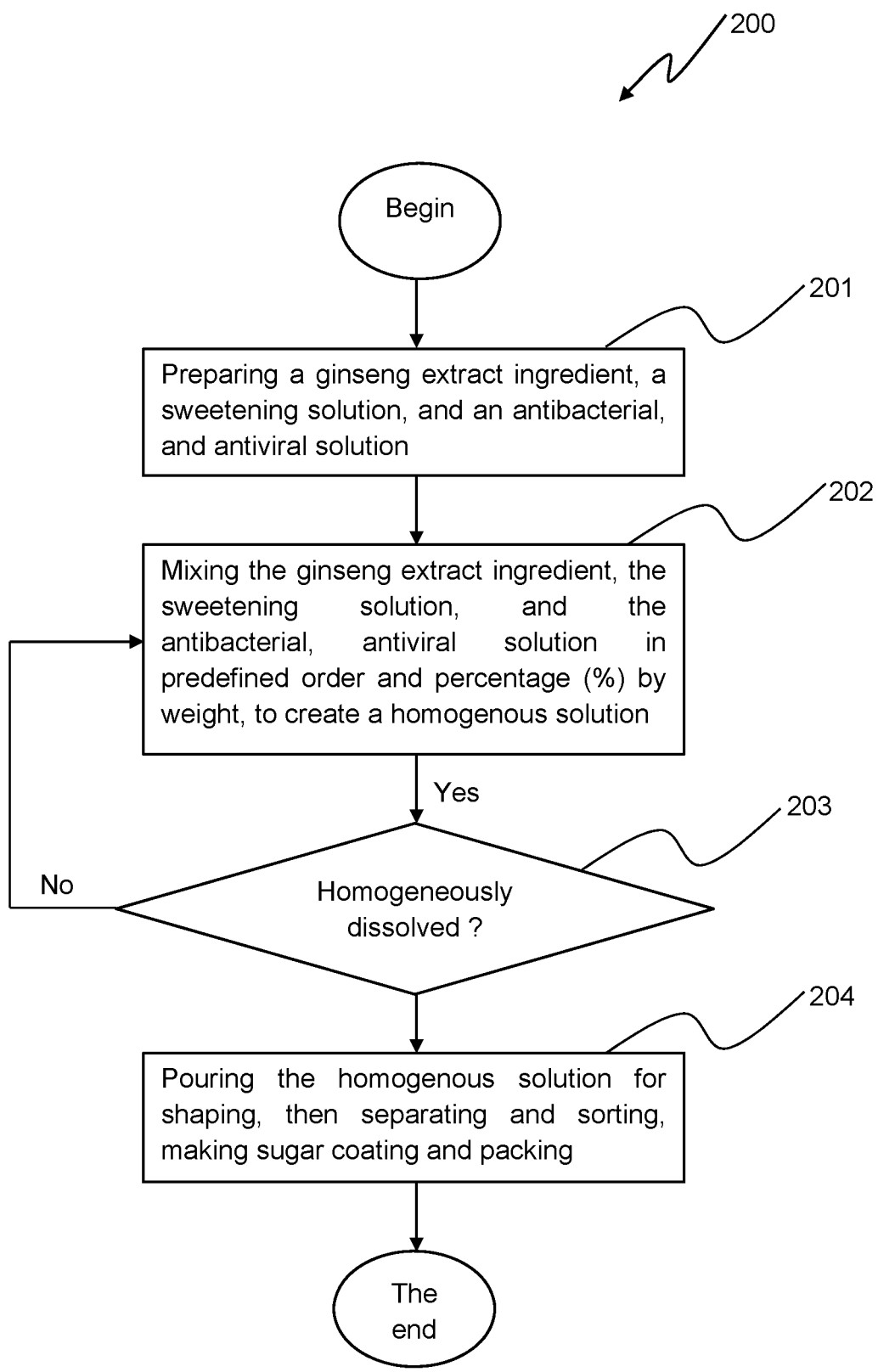
FIG. 2 is a flowchart illustrating a flowchart of a general method of manufacturing the ginseng candy composition containing the betel leaf extract in accordance with an exemplary embodiment of the present invention.

Now referring to FIG. 2, the method of manufacturing a ginseng candy composition containing the betel leaf extract 200 ("method 200") based on the above principle in accordance with an exemplary embodiment of the present invention. In particular, method 200 includes the following steps:

At step 201, preparing materials including the ginseng extract ingredient, the sweetening solution, the antibacterial, and antiviral solution; all the ingredients are carefully prepared and stored in separate instruments. The sweetener solution comprises the sweetener ingredient, the water ingredient, and ingredient D. According to the embodiment of the present invention, the sweetener solution is obtained by mixing the water ingredient with the sweetener ingredient combined with stirring 25-50 rpm in 10-15 minutes at a temperature of 75° C.-85° C., and heating to 147° C.; then adding ingredient D at 147° C. combined with stirring 25-50 rpm in 3-10 minutes.

According to the embodiment of the present invention, ingredient D includes the mixture of ginger-honey consisting of the ginger juice ingredient and the honey ingredient; and the mixture of lemon-kumquat-cinnamon consisting of the lemon juice ingredient, the kumquat juice ingredient, and the cinnamon ingredient.

In another preferred embodiment of the present invention, the mixture of ginger-honey is obtained by mixing ginger juice ingredient and the honey ingredient combined with stirring 30-40 rpm in five minutes, then fermentation for 30-180 minutes at a temperature of 25° C.-30° C.

In another preferred embodiment of the present invention, the mixture of lemon-kumquat-cinnamon is obtained by mixing the lemon juice ingredient with the cinnamon ingredient combined with stirring 30-40 rpm in five minutes, then adding the kumquat juice ingredient combined with stirring 30-40 rpm in five minutes and soaking for 10-15 minute.

In another preferred embodiment of the present invention, ingredient D includes the ginger juice ingredient, and the lemon juice ingredient.

According to the embodiment of the present invention, the antibacterial, antiviral solution is obtained by homogenizing mixing 4-allylpyrocatechol (APC) ingredient, the plant extracts/essential oils ingredients, and the betel leaf extract/essential oil ingredient in a specific order with a defined percentage (%) mentioned in the method 100; in which homogenizing mixing at room temperature.

At step 202, admixing the ginseng extract ingredient with the sweetener solution and the antibacterial, antiviral solution of a predetermined percentage (%) by weight, to create a homogenous solution. Step 202 is performed by a magnetic stirrer. Magnetic stirrer has been known in previous art so the description of the structure and its operating principle will not be described in detail in the invention.

At step 203, if the ginseng extract ingredient, the sweetener solution, and the antibacterial, antiviral solution are not uniformly dissolved in the homogenous solution, step 202 is repeated with a magnetic stirrer until homogenous conditions are reached.

Finally, at step 204, pouring the homogenous solution for shaping, then separating and sorting, making sugar coating and packing; to create a ginseng candy composition containing the betel leaf extract.

According to the embodiment of the present invention, the ginseng candy composition containing the betel leaf extract obtained by method 200 has the characteristic flavor of betel leaf and ginseng, is convenient, and can be used everywhere, even while traveling on trains, planes, and other types of transportation; or are working, studying, playing sports, etc.

According to the embodiment of the present invention, the ginseng candy composition of the present invention uses commonly food material or material with dual purposes of medicine and food, having high safety, and no side effects. At the same time contributes diversified products in the field of nutritional food and health care, suitable for all ages, convenience, large market demand with high application potential. Furthermore, the ginseng candy composition of ginsenoside components of ginseng are useful to facilitate ingestion by the consumer to be capable of contributing to the improvement of health and, with the increase of cultivated ginseng also agricultural development in related industries of ginseng may be performed so that it may be, and contributes to promoting the strengths of medicinal plants in general, and piper betel L. in particular.

TABLE 1

Some Citrus/*Citrus* fruits are used in the embodiment of the present invention

| No. | Citrus/Citrus fruits | Species | Collection region | Active Compounds | Mechanism of Action |
|---|---|---|---|---|---|
| 1 | Orange | *Citrus sinensis* | Vietnam | Limonene, β-myrcene, α-pinene, γ-terpinene, linalool, β-pinene | Antibacterial Anti-influenza virus Inhibit coronavirus replication |
| 2 | Lemon Lime | *Citrus lemon Citrus aurantifoli* | Vietnam | Limonene, β-myrcene, γ-terpinene, geranial, sabinene, neral, β-pinene, α-pinene | Antibacterial Inhibit virus replication |
| 3 | Kumquat | *Citrus japonica 'Japonica'* | Vietnam | C-glycosylated flavones, C-glycosylated flavones, O-glycosylated flavones, O-glycosylated flavones, flavonols, phenolic acids, chalcones | Antioxidant and Antimicrobial |
| 4 | Pomelo grapefruits | *Citrus maxima/Citrus grandis Citrus paradisi* | Vietnam | Limonene, β-myrcene, α-pinene, 7-geranoyloxycoumarin, β-pinene, γ-terpinene, linaloo | Antibacterial |
| 5 | Mandarin/ Clementina/ Tangerine | *Citrus reticulata L* | Vietnam | Limonene, γ-terpene, β-myrcene, α-pinene, decanal, β-pinene | Antibacterial |

TABLE 2

Mixed ingredients to creating a ginseng candy composition containing the betel leaf extract according to the embodiment of the invention

| | | Percentage (%) | | | |
|---|---|---|---|---|---|
| No. | Name of | Formula 1 (CT 1) | Preferably CT 1 | Formula 2 (CT 2) | Preferably CT 2 |
| 1 | A ginger juice ingredient | 0.5-1.5 | 1 | 0.5-1.5 | 1 |
| 2 | A honey ingredient | 2.5-7.5 | 5 | 0 | 0 |
| 3 | A lemon juice ingredient | 1.5-2 | 1.5 | 1.5-2 | 1.5 |
| 4 | A kumquat juice ingredient | 1.5-2 | 1.5 | 0 | 0 |
| 5 | A cinnamon ingredient | 0.3-0.4 | 0.3 | 0 | 0 |
| 6 | A plant extracts/essential oils ingredients | 0.5-1.5 | 0.9 | 0.5-1.5 | 0.9 |
| | + Lemongrass | | 0.2 | | 0.2 |
| | + Chinese liquorice/liquorice | | 0.2 | | 0.2 |
| | + Mint | | 0.5 | | 0.5 |
| 7 | A betel leaf extract/essential oil ingredient | 0.5 | 0.5 | 0.5 | 0.5 |
| 8 | A ginseng extract ingredient | 0.5 | 0.5 | 0.5 | 0.5 |
| 9 | A sweetener ingredient | 50-70 | 55-65 | 50-70 | 55-65 |
| 10 | 4-allylpyrocatechol (APC) ingredient | 0.16-0.17 | 0.16 | 0.16-0.17 | 0.16 |
| 11 | A water ingredient | rest | rest | rest | rest |

According to the embodiment of the present invention, the method of manufacturing 100 kilograms of the ginseng candy composition is listed in Table 3 below.

TABLE 3

Mixed ingredients of the ginseng candy composition in three examples according to the embodiment of the present invention

| Name of | Unit (Kg) | | |
| --- | --- | --- | --- |
| | Example 1 | Example 2 | Example 3 |
| A ginger juice ingredient | 1 | 1 | 1 |
| A honey ingredient | 5 | 0 | 0 |
| A lemon juice ingredient | 1.5 | 1.5 | 0 |
| A kumquat juice ingredient | 1.5 | 0 | 1.5 |
| A cinnamon ingredient | 0.5 | 0 | 0 |
| A lemongrass extracts/essential oil ingredient | 0.2 | 0.2 | 0.2 |
| A mint extracts/essential oil ingredient | 0.5 | 0.5 | 0.5 |
| A chinese liquorice/liquorice extracts/essential oil ingredient | 0.2 | 0.2 | 0.2 |
| A betel leaf extract/essential oil ingredient | 0.5 | 0.5 | 0.5 |
| A ginseng extract ingredient | 0.5 | 0.5 | 0.5 |
| A sweetener ingredient | 59 | 59 | 59 |
| 4-allylpyrocatechol (APC) ingredient | 0.17 | 0.17 | 0.17 |
| A water ingredient | Còn lại | Còn lại | Còn lại |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A ginseng candy composition containing the betel leaf A extract obtained from the process of forming a homogenous solution by mixing a ginseng extract ingredient with two different solutions comprising a sweetener solution, and an antibacterial, antiviral solution in the aforementioned order;

i) wherein said sweetener solution is obtained by mixing a water with a sweeteners combined with stirring 25-50 rpm in 10-15 minutes at a temperature of 75° C.-85° C., and heating to 147° C.; then adding a mixture D at 147° C. combined with stirring 25-50 rpm in 3-10 minutes;

the sweeteners are selected from the one or more of the following a refined sugar, a jaggery, a malt syrup, a starch molasses, a lactose, an alcohol sugar, and an additional sweeteners; wherein the additional sweetener are selected from a sugar, a sugar substitute, or a combination thereof;

the mixture D including a mixture of ginger-honey, and a mixture of lemon-kumquat-cinnamon;

the mixture of ginger-honey is obtained by mixing a ratio of a ginger juice and a honey solution having 1:5, combined with stirring 30-40 rpm in five minutes, then fermentation for 30-180 minutes at a temperature of 25° C.-30° C.;

the mixture of lemon-kumquat-cinnamon is obtained by mixing a lemon juice with a cinnamon powder combined with stirring 30-40 rpm in five minutes, then adding a kumquat juice combined with stirring 30-40 rpm in five minutes and soaking for 10-15 minute; wherein a ratio of the lemon juice:the kumquat juice: the cinnamon powder having 5:5:1;

ii) wherein said antibacterial, antiviral solution is obtained by sequential mixing a 4-allylpyrocatechol (APC) compound with a plant extracts/essential oils ingredients, and a betel leaf extract/essential oil;

the betel leaf extract/essential oil and the 4-allylpyrocatechol (APC) compound is extracted from fresh old betel leaves crushed/chopped/or not chopped, immersed are soaked in solvent, or saturated brine solution; wherein the total time from harvesting and preserving fresh old betel leaves from the betel nut tree must be less than 55 minutes;

the plant extracts/essential oils are ingredients selected from the one or more of the including chinese liquorice (*Glycyrrhiza uralensis* Fisch.), liquorice (*Glycyrrhiza Glabra* L.), tea (*Camellia sinensis*), holy basil (*Ocimum sanctum*), globe artichoke (*Cynara Scolymus* L.), roselle (*Hibiscus sabdariifa*), bitter melon (*Momordica charan*), basil (*Ocimum sanctum* L.), pomegranate (*Punica granatum* L.), chamber bitter (*Phyllanthus urinaria* L.), lemon balm (*Melissa officinalis*), mint (*Men-*

*tha haplocalyx* Briq.), horseradish tree (*Moringa oleifera* Lam.), white mulberry (*Morus alba* L.), broad-leaved plantain (*Plantago major* L.), areca nut palm (*Areca catechu* L.), apricot (*Prunus armeniaca* L.), lanxangia tsaoko (*Lanxangia tsaoko*), avocado (*Persea americana*), lemongrass (*Cymbopogon citratus, Cymbopogon winterianus* J., *Cymbopogon flexuosus* Stapf.), siamese ginger (*Alpinia officinarum*), red amaranth (*Amaranthus tricolor*), and tufuling (*Smilax glabra* Roxb);

iii) wherein said ginseng extract ingredient is extracted from ginseng parts including ginseng roots, ginseng stems, ginseng leaves, ginseng flowers, and ginseng fruits with seeds removed that cleaned, then crushed/chopped/or not chopped and soaked in solvent, or brine solution;

ginseng roots having at least 6 years old; ginseng stems, ginseng leaves, ginseng flowers and ginseng fruits with seeds removed having at least 3 years old;

the ginseng parts are selected from the one or more in the genus *Panax* of the including *Panax notoginseng, Panax bipinnatifidus*; Korean ginseng, ginseng, red ginseng (*Panax ginseng*), *Panax japonicus*; American ginseng, Atlantic ginseng (*Panax quinquefolius*); Ngoc Linh ginseng, Vietnamese ginseng (*Panax vietnamensis*), *Panax wangianus, Panax zingiberebsis*, Himalayan ginseng (*Panax pseudoginseing*), and *Panax stipuleanatus;* wherein a ratio of the betel leaf extract/essential oil and the 4-allylpyrocatechol (APC) compound, and the ginseng extract ingredient having 3:1:3.

2. The composition of claim 1, wherein the plant extracts/essential oils ingredients including chinese liquorice (*Glycyrrhiza uralensis* Fisch.), liquorice (*Glycyrrhiza Glabra* L.), mint (*Mentha haplocalyx* Briq.), and lemongrass (*Cymbopogon citratus, Cymbopogon winterianus* J., *Cymbopogon flexuosus* Stapf.).

3. The composition of claim 1, wherein the ginseng extract ingredient further comprising extracted from a ginseng biomass in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, and Vietnamese ginseng (*Panax vietnamensis*).

4. The composition of claim 1, wherein the ginseng extract ingredient further comprising a commercial ginseng products in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, and Vietnamese ginseng (*Panax vietnamensis*).

5. The composition of claim 1, wherein the ginseng parts are selected from the one or more in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, and Vietnamese ginseng (*Panax vietnamensis*).

6. The composition of claim 1, wherein the composition comprising:
(a) the sweeteners having 50%-70% by weight including 23% by weight of the malt syrup;
(b) the ginger juice having 0.5%-1.5% by weight;
(c) the honey solution having 2.5%-7.5% by weight;
(d) the lemon juice having 1.5%-2% by weight;
(e) the kumquat juice having 1.5%-2% by weight;
(f) the cinnamon powder having 0.3%-0.4% by weight;
(g) the 4-allylpyrocatechol (APC) compound having 0.16%-0.17% by weight;
(h) the plant extracts/essential oils ingredients having 0.5%-1.5% by weight;
(j) the betel leaf extract/essential oil having 0.5% by weight;
(k) the ginseng extract ingredient having 0.5% by weight; and
(l) the remainder is the water.

7. The composition of claim 6, wherein the composition comprising:
(a) the sweeteners having 55%-65% by weight including 23% by weight of the malt syrup;
(b) the ginger juice having 1% by weight;
(c) the honey solution having 5% by weight;
(d) the lemon juice having 1.5% by weight;
(e) the kumquat juice having 1.5% by weight;
(f) the cinnamon powder having 0.3% by weight;
(g) the 4-allylpyrocatechol (APC) compound having 0.16% by weight;
(h) the plant extracts/essential oils ingredients having 0.9% by weight including 0.2% by weight of a lemongrass extracts/essential oil, 0.5% by weight of a mint extracts/essential oil, and 0.2% by weight of a chinese liquorice/liquorice extracts/essential oil;
(j) the betel leaf extract/essential oil having 0.5% by weight;
(k) the ginseng extract ingredient having 0.5% by weight; and
(l) the remainder is the water.

8. A ginseng candy composition containing the betel leaf extract obtained from the process of forming a homogenous solution by mixing a ginseng extract ingredient with two different solutions comprising a sweetener solution, and an antibacterial, antiviral solution in the aforementioned order;

i) wherein said sweetener solution is obtained by mixing a water with a sweeteners combined with stirring 25-50 rpm in 10-15 minutes at a temperature of 75° C.-85° C., and heating to 147° C.; then adding a mixture D at 147° C. combined with stirring 25-50 rpm in 3-10 minutes;

the sweeteners are selected from the one or more of the following a refined sugar, a jaggery, a malt syrup, a starch molasses, a lactose, an alcohol sugar, and an additional sweeteners; wherein the additional sweetener are selected from a sugar, a sugar substitute, or a combination thereof;

the mixture D including a ginger juice, and a lemon juice;

ii) wherein said antibacterial, antiviral solution is obtained by sequential mixing a 4-allylpyrocatechol (APC) compound with a plant extracts/essential oils ingredients, and a betel leaf extract/essential oil;

the betel leaf extract/essential oil and the 4-allylpyrocatechol (APC) compound is extracted from fresh old betel leaves crushed/chopped/or not chopped, immersed are soaked in solvent, or brine solution; wherein the total time from harvesting and preserving fresh old betel leaves from the betel nut tree must be less than 55 minutes;

the plant extracts/essential oils ingredients are selected from the one or more of the including chinese liquorice (*Glycyrrhiza uralensis* Fisch.), liquorice (*Glycyrrhiza Glabra* L.), tea (*Camellia sinensis*), holy basil (*Ocimum sanctum*), globe artichoke (*Cynara Scolymus* L.), roselle (*Hibiscus sabdariffa*), bitter melon (*Momordica charan*), basil (*Ocimum sanctum* L.), pomegranate (*Punica granatum* L.), chamber bitter (*Phyllanthus urinaria* L.), lemon balm (*Melissa officinalis*), mint (*Men-*

*tha haplocalyx* Briq.), horseradish tree (*Moringa oleifera* Lam.), white mulberry (*Morus alba* L.), broad-leaved plantain (*Plantago major* L.), areca nut palm (*Areca catechu* L.), apricot (*Prunus armeniaca* L.), lanxangia tsaoko (*Lanxangia tsaoko*), avocado (*Persea americana*), lemongrass (*Cymbopogon citratus, Cymbopogon winterianus* J., *Cymbopogon flexuosus* Stapf.), siamese ginger (*Alpinia officinarum*), red amaranth (*Amaranthus tricolor*), and tufuling (*Smilax glabra* Roxb);

iii) wherein said ginseng extract ingredient is extracted from ginseng parts including ginseng roots, ginseng stems, ginseng leaves, ginseng flowers, and ginseng fruits with seeds removed that cleaned, then crushed/chopped/or not chopped and soaked in solvent, or or brine solution;

ginseng roots having at least 6 years old; ginseng stems, ginseng leaves, ginseng flowers and ginseng fruits with seeds removed having at least 3 years old;

the ginseng parts are selected from the one or more in the genus *Panax* of the including *Panax notoginseng, Panax bipinnatifidus*; Korean ginseng, ginseng, red ginseng (*Panax ginseng*), *Panax japonicus*; American ginseng, Atlantic ginseng (*Panax quinquefolius*); Ngoc Linh ginseng, Vietnamese ginseng (*Panax vietnamensis*), *Panax wangianus, Panax zingiberebsis*, Himalayan ginseng (*Panax pseudoginseing*), and *Panax stipuleanatus;* wherein a ratio of the betel leaf extract/essential oil ingredient and the 4-allylpyrocatechol (APC) compound, and the ginseng extract ingredient having 3:1:3.

9. The composition of claim 8, wherein the plant extracts/essential oils ingredients including chinese liquorice (*Glycyrrhiza uralensis* Fisch.), liquorice (*Glycyrrhiza Glabra* L.), mint (*Mentha haplocalyx* Briq.), and lemongrass (*Cymbopogon citratus, Cymbopogon winterianus* J., *Cymbopogon flexuosus* Stapf.).

10. The composition of claim 8, wherein the ginseng extract ingredient further comprising extracted from a ginseng biomass in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, and Vietnamese ginseng (*Panax vietnamensis*).

11. The composition of claim 8, wherein the ginseng extract ingredient further comprising a commercial ginseng products in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Linh ginseng, and Vietnamese ginseng (*Panax vietnamensis*).

12. The composition of claim 8, wherein the ginseng parts are selected from the one or more in the genus *Panax* of the including *Panax notoginseng*; Korean ginseng, ginseng, red ginseng (*Panax ginseng*); Japanese ginseng (*Panax japonicus*); American ginseng, Atlantic ginseng (*Panax quinquefolius*); Ngoc Unh *ginseng*, and Vietnamese ginseng (*Panax vietnamensis*).

13. The composition of claim 8, wherein the composition comprising:
(A) the sweeteners having 50%-70% by weight including 23% by weight of the malt syrup;
(B) the ginger juice having 0.5%-1.5% by weight;
(C) the lemon juice having 1.5%-2% by weight;
(D) the 4-allylpyrocatechol (APC) compound having 0.18%-0.17% by weight;
(E) the plant extracts/essential oils ingredients having 0.5%-1.5% by weight;
(F) the betel leaf extract/essential oil having 0.5% by weight;
(G) the ginseng extract ingredient having 0.5% by weight; and
(H) the remainder is the water.

14. The composition of claim 13, wherein the composition comprising:
(A) the sweeteners having 55%-65% by weight including 23% by weight of the malt syrup;
(B) the ginger juice having 1% by weight;
(C) the lemon juice having 1.5% by weight;
(D) the 4-allylpyrocatechol (APC) compound having 0.16% by weight;
(E) the plant extracts/essential oils ingredients having 0.9% by weight including 0.2% by weight of a lemongrass extracts/essential oil, 0.5% by weight of a mint extracts/essential oil, and 0.2% by weight of a chinese liquorice/liquorice extracts/essential oil;
(F) the betel leaf extract/essential oil having 0.5% by weight;
(G) the ginseng extract ingredient having 0.5% by weight; and
(H) the remainder is the water.

\* \* \* \* \*